United States Patent [19]

Ray et al.

[11] 4,425,914

[45] Jan. 17, 1984

[54] HUMIDIFIER-INJECTOR FOR JET VENTILATOR

[75] Inventors: Cole Ray; John Vincent, both of New York; Clifford Small, Jamaica, all of N.Y.

[73] Assignee: Memorial Hospital for Cancer and Allied Diseases, New York, N.Y.

[21] Appl. No.: 233,245

[22] Filed: Feb. 10, 1981

[51] Int. Cl.³ ............................................. A61M 16/00
[52] U.S. Cl. ........................... 128/200.14; 128/203.12; 261/DIG. 65; 261/78 A; 239/426; 239/434
[58] Field of Search ....................... 128/200.14, 200.21, 128/200.22, 205.24, 204.21, 207.14, 207.15, 203.12; 261/DIG. 65, 78 A; 239/426, 434

[56] References Cited

U.S. PATENT DOCUMENTS

| 310,999 | 1/1885 | Hibbard | 128/200.22 |
| 423,198 | 3/1890 | Windolph . | |
| 1,554,219 | 9/1925 | Kitchen | 128/200.21 |
| 2,906,513 | 9/1959 | Tabor | 261/78 A |
| 3,182,659 | 5/1965 | Blount | 128/200.21 |
| 3,470,869 | 10/1969 | Fenton et al. . | |
| 4,026,285 | 5/1977 | Jackson | 128/200.14 |
| 4,030,492 | 6/1977 | Simbruner | 128/200.21 |
| 4,108,178 | 8/1978 | Betush | 128/224 |
| 4,265,237 | 5/1981 | Schwanbom et al. | 128/204.25 |
| 4,270,530 | 6/1981 | Baum et al. | 128/204.25 |

Primary Examiner—Henry J. Recla
Attorney, Agent, or Firm—Felfe & Lynch

[57] ABSTRACT

A humidifier-injector for use with a jet ventilator.

11 Claims, 5 Drawing Figures

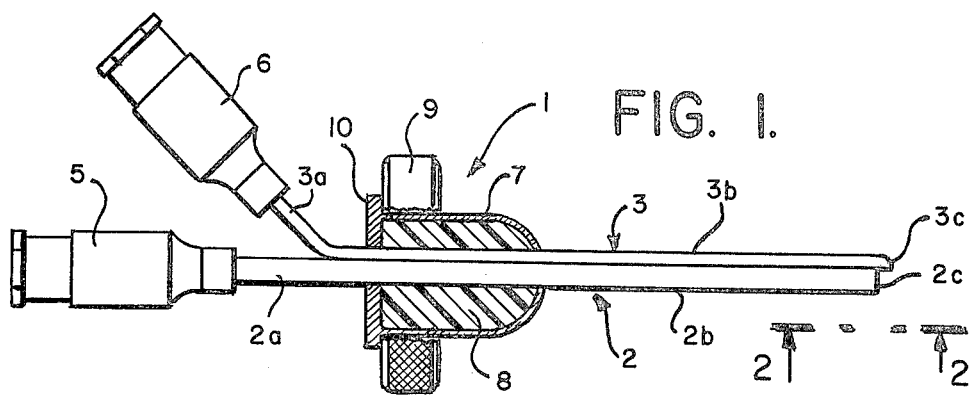
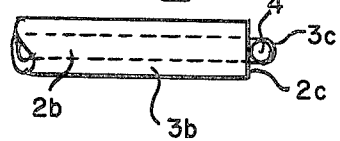
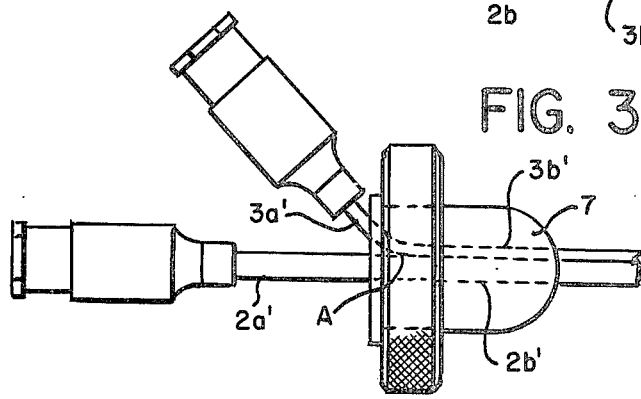
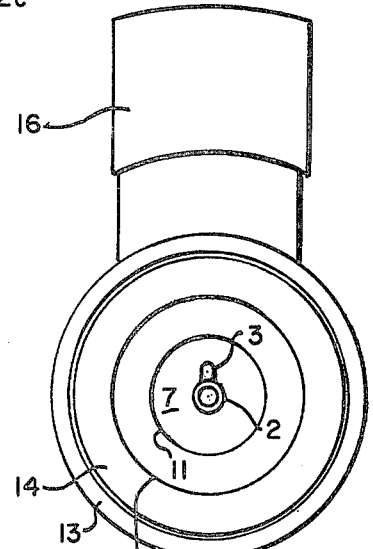
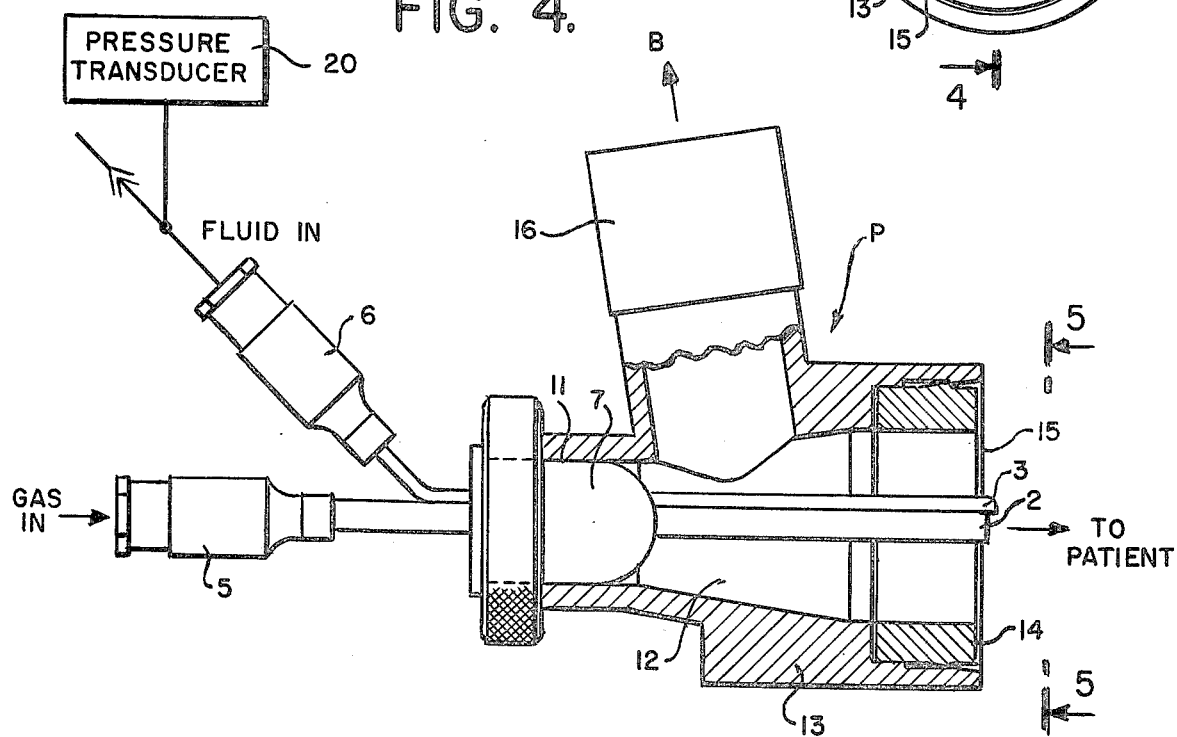

HUMIDIFIER-INJECTOR FOR JET VENTILATOR

BACKGROUND OF THE INVENTION

The present invention relates to a humidifier-injector for a jet ventilator.

Jet ventilators, and in particular high frequency jet ventilators, operate by introducing into the airway of a patient, a relatively small volume of gas on the order of 100 ml at a high velocity by way of a short pulse of, for example, 130 ms. This high speed stream will entrain and accelerate a larger volume of stationary gas through the open airway. The pulse duty cycle of approximately 33% on the 66% off is repeated up to several hundred times per minute resulting in a relatively large flow per minute in and out of the lungs, i.e., 18–30 LPM.

This high frequency low volume method of ventilation is insensitive to leaks or openings in the airway and does not result in the generation of high airway pressures as does conventional high volume low frequency ventilation. Clinical experience has shown that both the jet gas and the entrained gas must be humidified to prevent dessication of and damage to the mucosal lining of the airways.

Prior art high frequency jet ventilation systems have effected humidification of the high speed gas stream by conditioning the jet gas before injection, however this has the disadvantage of increasing the device comlexity.

SUMMARY OF THE INVENTION

The object of the present invention is to overcome the disadvantages of the prior art.

Another object of the present invention is to provide a simple humidifier-injector which serves to inject gas and humidify it in a reliable and efficient manner.

Another important advantage of the humidifier-injector of the present invention is that it is capable of serving as a pressure transmission line to facilitate an alarm function when utilized in a high-frequency jet ventilation system as described in copending U.S. application Ser. No. 233,244, filed Feb. 10, 1981. In this context, the airway cannula pressure transducer can be connected in series with the humidifying fluid input to the humidifier-injector according to the present invention so as to get an accurate and direct indication of the pressure at the cannula tip for the alarm system described in the aforesaid copending application.

These and other objects of the present invention are achieved according to the present invention by an injector humidifier comprising a first inlet receptive of a source of high frequency pulses of high velocity gas, a second inlet receptive of a humidifying fluid, a first pipe having its input end in communication with the first inlet and its output end configured to direct the flow of gas parallel to the longitudinal axis thereof and means in communication with the second inlet for directing humidifying fluid adjacent to the output end of the first pipe and substantially perpendicularly to the longitudinal axis thereof and thereby the flow of gas directed thereby.

Other advantages of the present invention will become more apparent from the detailed description of the invention with reference to the attached drawings wherein:

BRIEF DESCRIPTION OF THE DRAWINGS

FIG. 1 is a partial sectional view of the injector-humidifier according to the present invention;

FIG. 2 is a view along line 2—2 of FIG. 1;

FIG. 3 is a side view of an alternative embodiment of the device shown in FIG. 1;

FIG. 4 is a partial sectional view along line 4—4 of FIG. 5 showing the injector-humidifier in an airway connector; and FIG. 5 is a view along line 5—5 in FIG. 4.

DETAILED DESCRIPTION OF THE PREFERRED EMBODIMENTS

Referring now to FIGS. 1-2, the humidifier-injector 1 includes a first inlet 5 receptive of a source of high frequency pulses of high velocity gas and a first pipe 2 having its input end 2a in communication with the first inlet 5 and its output end 2c configured to direct the flow of gas parallel to the longitudinal axis thereof.

A second inlet 6 is receptive of a humidifying fluid and is connected to means including pipe 3 for directing humidifying fluid adjacent to the output end 2c of the first pipe 2 and substantially perpendicularly to the longitudinal axis thereof and thereby the flow of gas directed thereby.

The pipe 3 is connected at its input end 3a to the inlet 6 and includes an intermediate section 3b which extends parallel to intermediate section 2b of pipe 2 and abuts same as shown. Pipe 3 has an end portion 3c which projects slightly from the output end 2c of pipe 2 and which has aperture 4 (FIG. 2) which faces perpendicularly to the longitudinal axis of the pipe 2 so as to direct the humidifying fluid perpendicularly to gas flowing out of the output end 2c of pipe 2.

The two pipes 2, 3 are mounted in a cup-shaped fitting 7 centrally thereof and are fixed in place by filling the cup-shaped member 7 with a cement 8 such as an epoxy resin. The cup-shaped fitting 7 includes a top flange 10 and a knurled gripping ring 9 disposed therearound. The gripping ring 9 enables the fitting 7 to be inserted and removed in a connector as will be described hereinafter.

As shown in FIG. 1, the nonabutting portions 2a and 3a of pipes 2 and 3 approach each other at an acute angle from inlets 5 and 6. In an improvement of the present invention as shown in FIG. 3, the point A at which the nonabutting portions 2a' and 3a' converge and thereafter abut at 2b' and 3b', is disposed within the cup-shaped member 7 so that the cement 8 encapsulates a portion of the nonabutting sections 2a' and 3a' whereby a more reliable fixing of the pipes 2 and 3 can be achieved in the fitting 7.

Referring now to FIGS. 4 and 5, the humidifier-injector is shown mounted in a Portex ® swivel type disposable tracheostomy/endotracheal tube connector P.

The connector P includes a body 13 of rigid plastic which defines a venting chamber 12 therein and which has an inlet 11 receptive of the fitting 7 so as to dispose the pipes 2, 3 concentrically within the venting chamber 12 and at the center of outlet opening 15 of the swiveling member 14 therein. The connector P also includes a venting outlet 16 which, when used in a jet ventilating system is connected to a source of humidified air and/or oxygen.

In a specific example of the present invention when used with the Portex disposable swivel connector, pipe 2 comprises a cylindrical stainless steel first tube having an inner diameter of 1.6 mm and a length of 52.5 mm. Pipe 3 comprises a second tube brazed in parallel to the first tube and having an inner diameter of 0.8 mm and a length of 54.5 mm. The outlet of the first mentioned tube is cut at right angles while the outlet end of the longer smaller second tube is drawn so that its distal opening is directed at 90° across the opening of the first tube.

The inlets 5 and 6 are standard luerlok needle hubs and the fitting 7 is a 9.5 mm plug which is friction fit into the commercially available Portex connector thus aligning the injector tubes concentrically with respect to the longitudinal axis of the tracheostomy or endotracheal tube fitted at the outlet opening 15 of the connector.

In operation, pipe 2 is connected to a jet ventilator which is the source of high frequency pulses of high velocity gas and pipe 3 is connected to a positive displacement intravenous infusion pump. In a particular example the pump is set to deliver 44 mg of water or 0.9% saline for each liter per minute of jet gas flow to pipe 3, since this is the amount of water necessary to saturate 1 liter of air at 37° C. (body temperature). The jet ventilator which delivers the pulses of high velocity gas is adjusted and activated, gating a gas pressure of 15–45 psig to pipe 2 in pulses. The high velocity gas stream impacting on the water drops as they are pumped from the side hole 4 of pipe 3 aerosolizes the water and carries it distally into the airway with the entrained gas.

The humidifier injector according to the present invention is particularly advantageous in that a pressure transducer 20 can be connected at the inlet 6 to sense the pressure pulses arriving via inlet 5. As explained in the aforementioned copending application directed to the jet ventilating system, the pressure transducer 20 produces a signal marking the appearance of each jet pulse at the inlet 5 and this signal can be suitably conditioned to operate an alarm system within the ventilator which detects both the presence and amplitude of the pulse.

It will be appreciated that the instant specification and example are set forth by way of illustration and not limitation, and that various modifications and changes may be made without departing from the spirit and scope of the present invention.

What is claimed is:

1. A humidifier-injector for a jet ventilator and adapted to mount to an airway connector, said humidifier-injector comprising a first pipe with means for receiving and conducting high frequency pulses of high velocity gas and means for directing said gas exiting said first pipe; a second pipe with means for receiving and conducting a humidifying fluid and means for directing said fluid exiting said second pipe; and sealing means intermediate the receiving and directing means of said first and second pipes, wherein:

(a) said receiving means of said first pipe permits gas-tight communication between said conducting means of said first pipe and a source of high frequency pulses of high velocity gas;

(b) said receiving means of said second pipe permits fluid-tight communication between said conducting means of said second pipe and a source of humidifying fluid;

(c) said directing means of said second pipe directs said exiting fluid such that said fluid is impacted by the flow of said gas exiting said first pipe;

(d) said sealing means comprising first and second cylindrical portions, each of said cylindrical portions being substantially coaxial with said first and second pipe conducting means, wherein:

(1) said first cylindrical portion is of small diameter than said second cylindrical portion, extends from a first point on said conducting means to a remote point intermediate said second cylindrical portion and said first and second pipe directing means, and is adapted to fit into a cylindrical inlet in an airway connector; and (2) said second cylindrical portion is adjacent said first cylindrical portion, is located intermediate the remote point of said first cylindrical portion and said first and second pipe receiving means, and coacts with said first cylindrical portion to (i) locate and maintain said first and second pipe conducting means coaxially within said airway connector inlet and (ii) to effect a seal between the interior of said airway connector inlet and the atmosphere.

2. The humidifier-injector according to claim 1, wherein said second pipe means for directing humidifying fluid comprises an aperature facing perpendicularly to the longitudinal axis of said first pipe directing means.

3. The humidifier-injector according to claim 2, wherein said second pipe conducting means has a section thereof extending parallel to said first pipe conducting means and abutting same.

4. The humidifier-injector according to claim 3, wherein the abutting section of said second pipe conducting means extends slightly past the directing means of said first pipe and said second pipe directing means comprises an aperture disposed in the side of said second pipe closest to said first pipe directing means.

5. The humidifier-injector according to claim 4, said sealing means comprising a cup-shaped fitting.

6. The humidifier-injector according to claim 5, wherein said second pipe conducting means includes an intermediate section, between the receiving means thereof and said abutting section, extending towards said first pipe at an acute angle to the longitudinal axis of the first pipe and wherein a portion of said intermediate section and a non-abutting section of said first pipe conducting means are encapsulated by said sealing means.

7. The humidifier-injector according to claim 5 in combination with an airway connector having inlet means receptive of said sealing means in a force-fit gas-tight manner, a venting chamber connected thereto, and a patient connection port, said first and second pipes extending from said inlet means, through said venting chamber and to said patient connection port.

8. The humidifier-injector according to claim 2, wherein the cross sectional area of said first pipe is greater than that of said second pipe.

9. A humidifier-injector according to claim 1 or 7 in combination with a pressure transducer communicating with said second pipe receiving means and connecting means intermediate said transducer and said receiving means, whereby pressure pulses arriving at said first pipe directing means may be sensed via said second pipe directing means.

10. A method of jet ventilating a patient comprising the steps of providing a humidifier-injector according to claim 9 in communication with the patient's airway; applying pulses of gas to said first pipe receiving means; applying humidifying fluid to said second pipe receiving means; and sensing the fluid pressure at said first pipe directing means via said second pipe directing means.

11. A method of jet ventilating a patient comprising the steps of providing a humidifier-injector according to claim 1 or 7 in communication with the patient's airway; applying pulses of gas to said first pipe receiving means; and applying humidifying fluid to said second pipe receiving means.

* * * * *